(12) United States Patent
Reiter

(10) Patent No.: US 9,370,337 B2
(45) Date of Patent: Jun. 21, 2016

(54) WIREBONDING FIXTURE AND CASTING MOLD

(71) Applicant: Volcano Corporation, San Diego, CA (US)

(72) Inventor: Michael Reiter, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 3 days.

(21) Appl. No.: 14/143,843

(22) Filed: Dec. 30, 2013

(65) Prior Publication Data

US 2014/0184026 A1 Jul. 3, 2014

Related U.S. Application Data

(60) Provisional application No. 61/747,599, filed on Dec. 31, 2012.

(51) Int. Cl.
| | |
|---|---|
| *A61B 8/00* | (2006.01) |
| *B29C 45/03* | (2006.01) |
| *H03H 3/02* | (2006.01) |
| *B06B 1/06* | (2006.01) |
| *A61B 8/12* | (2006.01) |

(52) U.S. Cl.
CPC ............. *A61B 8/4483* (2013.01); *B06B 1/0651* (2013.01); *B06B 1/0688* (2013.01); *H03H 3/02* (2013.01); *A61B 8/12* (2013.01); *A61B 8/445* (2013.01); *B29C 45/03* (2013.01); *Y10T 29/42* (2015.01); *Y10T 29/4957* (2015.01)

(58) Field of Classification Search
USPC ........................................................ 164/343
See application file for complete search history.

(56) References Cited

U.S. PATENT DOCUMENTS

| | | | | |
|---|---|---|---|---|
| 4,158,910 | A | * | 6/1979 | Hanas et al. ..................... 29/469 |
| 4,668,460 | A | * | 5/1987 | Ongena ............... B29C 37/0028 264/255 |
| 5,770,941 | A | * | 6/1998 | Van Den Berg ......... 324/207.16 |
| 5,935,502 | A | * | 8/1999 | Ferri ................ B29C 45/14655 257/E21.504 |
| 5,943,558 | A | * | 8/1999 | Kim ..................... H01L 23/057 257/E23.066 |
| 6,196,824 | B1 | * | 3/2001 | Foltuz et al. .................. 425/190 |
| 6,423,102 | B1 | * | 7/2002 | Fukunaga ............. B25B 11/005 269/21 |
| 2008/0304729 | A1 | | 12/2008 | Peszynski |
| 2009/0192388 | A1 | | 7/2009 | Yamada et al. |
| 2010/0160788 | A1 | * | 6/2010 | Davies et al. ................. 600/467 |
| 2010/0168583 | A1 | | 7/2010 | Dausch et al. |
| 2012/0056511 | A1 | | 3/2012 | Sakai |
| 2012/0262796 | A1 | | 10/2012 | Ferguson et al. |

OTHER PUBLICATIONS

International Search Report and Written Opinion received in corresponding Patent Cooperation Treaty Application No. PCT/US2013/078280 dated Apr. 21, 2014, 12 pages.

* cited by examiner

*Primary Examiner* — Devang R Patel
(74) *Attorney, Agent, or Firm* — Haynes and Boone, LLP

(57) ABSTRACT

The present disclosure involves a method and apparatus for attaching two electrical dies by wire bonding and then encasing the assembly in a protective casting that works by arranging two dies into a fixture conducive to wire bonding. Doped epoxy may be immediately dispensed over the assembly to form a near-net-shape protective cover, or Drive Can.

20 Claims, 9 Drawing Sheets

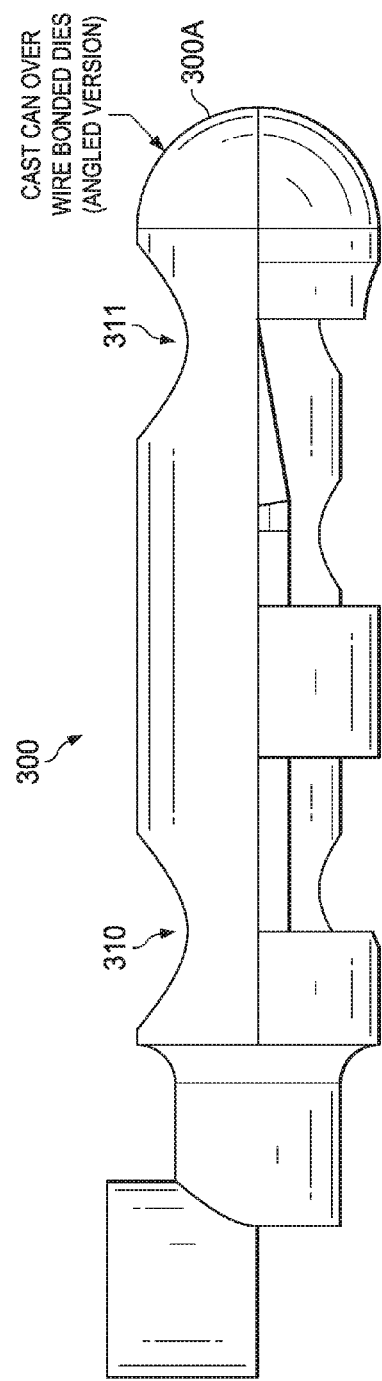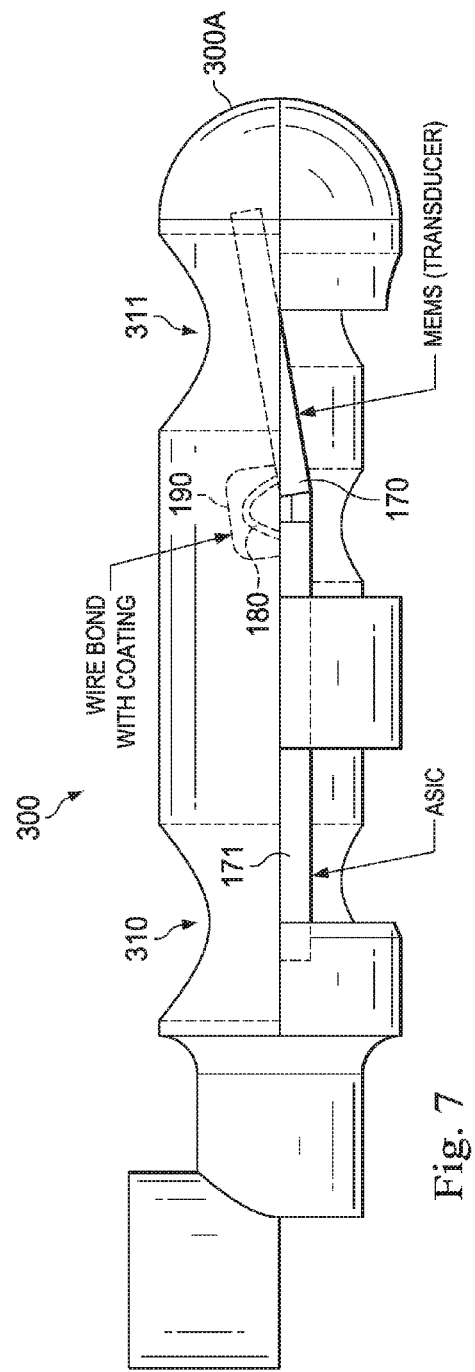

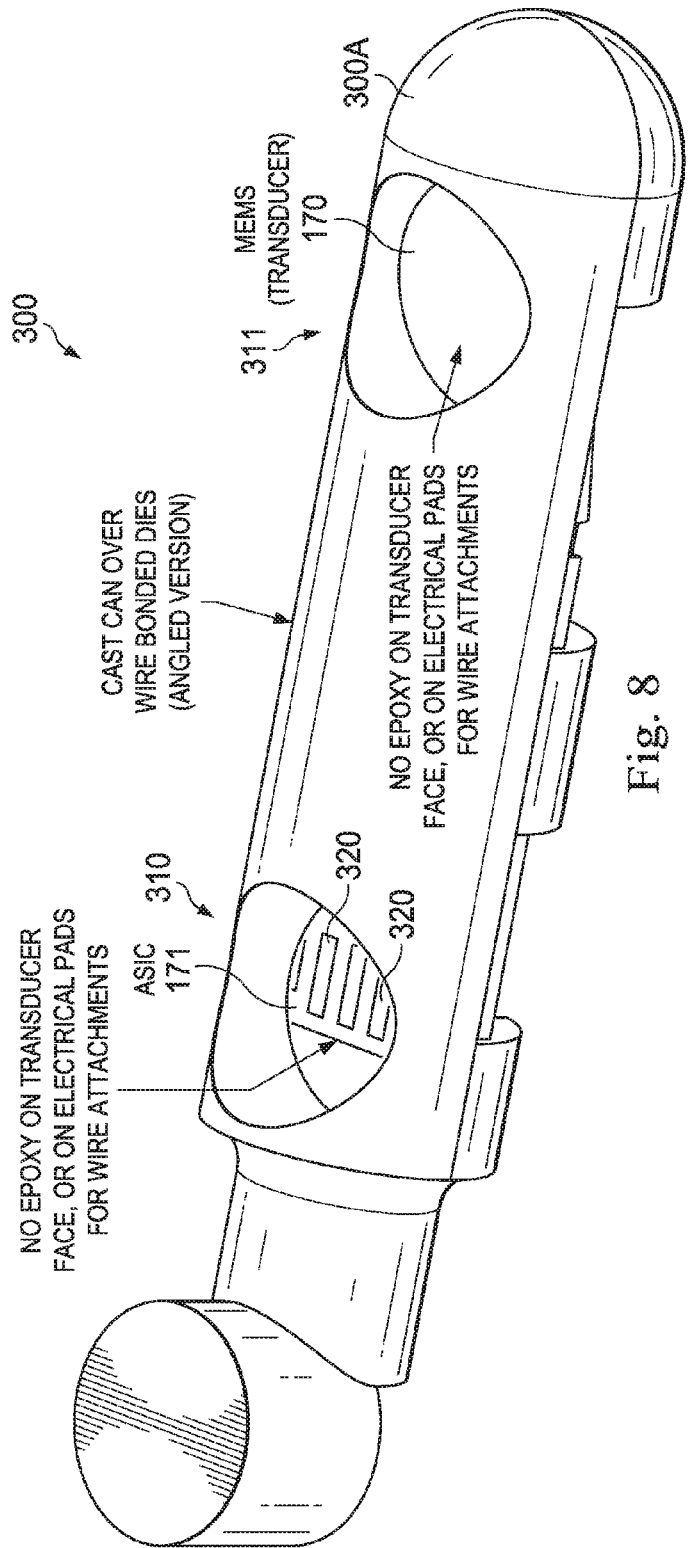

WIREBONDING FIXTURE AND CASTING MOLD

CROSS-REFERENCE TO RELATED APPLICATIONS

This application claims priority to Provisional U.S. Patent Application No. 61/747,599, filed Dec. 31, 2012, and entitled "WIREBONDING FIXTURE AND CASTING MOLD," the disclosure of which is hereby incorporated by reference in its entirety.

TECHNICAL FIELD

The present disclosure relates generally to intravascular ultrasound (IVUS) imaging, and in particular, to a wirebonding fixture and casting mold for an IVUS ultrasound transducer, such as a piezoelectric micromachined ultrasound transducer (PMUT), used for IVUS imaging.

BACKGROUND

Intravascular ultrasound (IVUS) imaging is widely used in interventional cardiology as a diagnostic tool for assessing a vessel, such as an artery, within the human body to determine the need for treatment, to guide intervention, and/or to assess its effectiveness. An IVUS imaging system uses ultrasound echoes to form a cross-sectional image of the vessel of interest. Typically, IVUS imaging uses a transducer on an IVUS catheter that both emits ultrasound signals (waves) and receives the reflected ultrasound signals. The emitted ultrasound signals (often referred to as ultrasound pulses) pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound signals (often referred to as ultrasound echoes) to produce a cross-sectional image of the vessel where the IVUS catheter is located.

IVUS catheters typically employ one or more transducers to transmit ultrasound signals and receive reflected ultrasound signals. However, conventional catheters may create a separate wire-die sub assembly that is then placed into a stainless steel shell (also referred to as a can) and then epoxied with a specially doped epoxy. This shell or can is shaped to prevent acoustic echo off of the metal can. Preventing separation of the transducer from the can is important. However, this is not always achieved by conventional techniques.

Therefore, while conventional methods of producing and assembling transducers are generally adequate for their intended purposes, they have not been entirely satisfactory in every aspect.

SUMMARY

The present disclosure provides a method and apparatus for attaching two electrical dies by wire bonding and then encasing the assembly in a protective casting that works by arranging two dies into a fixture conducive to wire bonding. Doped epoxy may be immediately dispensed over the assembly to form a near-net-shape protective cover, or Drive Can.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 6-9 are various diagrammatic perspective and cross-sectional views of a transducer assembly fabricated by the bonding apparatus shown in FIGS. 2-5 according to various aspects of the present disclosure.

DETAILED DESCRIPTION

Figure 1:
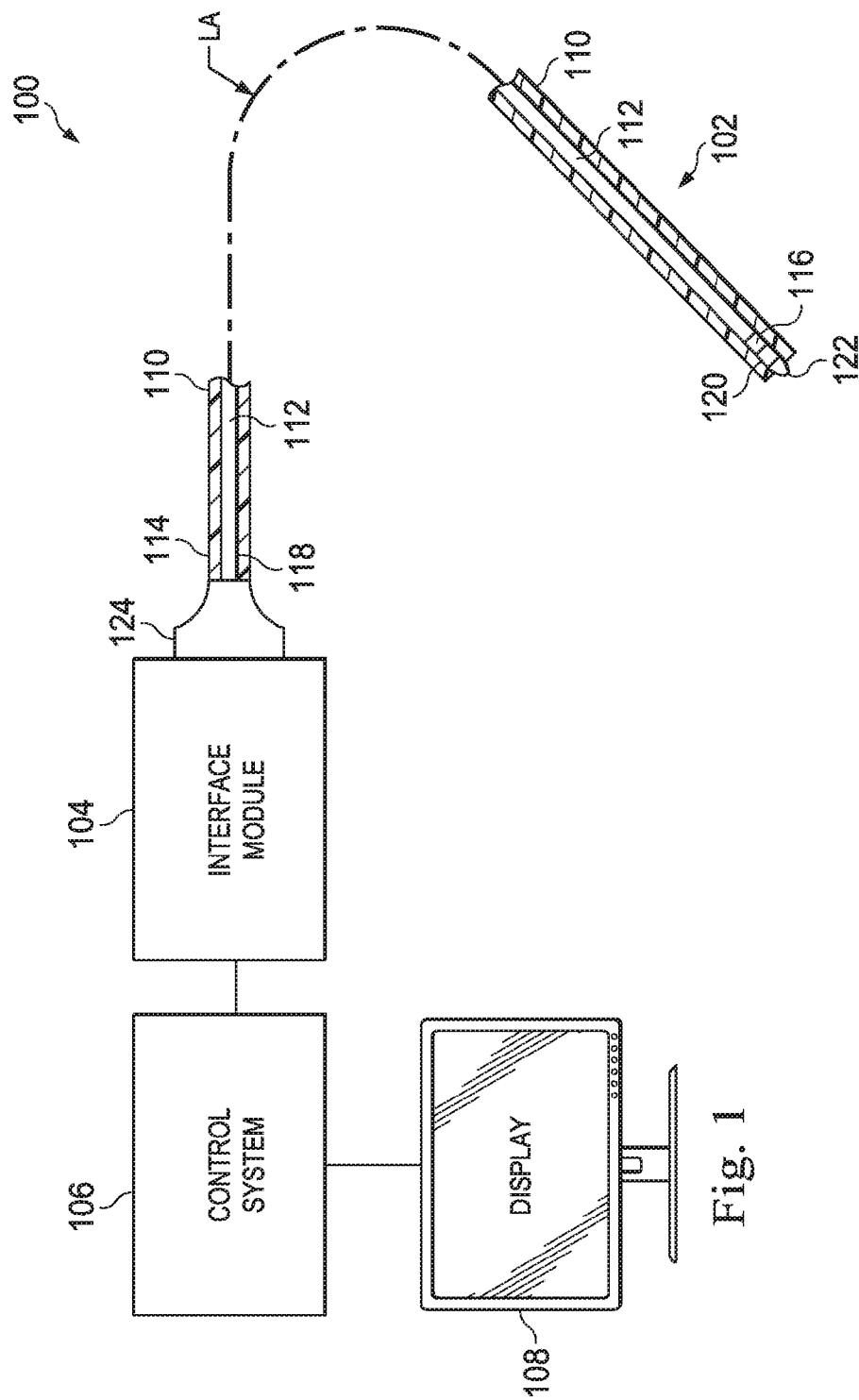
FIG. 1 is a schematic illustration of an intravascular ultrasound (IVUS) imaging system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application. In some embodiments, the ultrasound imaging system includes an intravascular imaging system. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

There are primarily two types of catheters in common use today: solid-state and rotational. An exemplary solid-state catheter uses an array of transducers (typically 64) distributed around a circumference of the catheter and connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector.

An exemplary rotational catheter includes a single transducer located at a tip of a flexible driveshaft that spins inside a sheath inserted into the vessel of interest. The transducer is typically oriented such that the ultrasound signals propagate generally perpendicular to an axis of the catheter. In the typical rotational catheter, a fluid-filled (e.g., saline-filled) sheath protects the vessel tissue from the spinning transducer and driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer.

FIG. 1 is a schematic illustration of an ultrasound imaging system 100 according to various aspects of the present disclosure. In some embodiments, the ultrasound imaging system 100 includes an intravascular ultrasound imaging system (IVUS). The IVUS imaging system 100 includes an IVUS catheter 102 coupled by a patient interface module (PIM) 104 to an IVUS control system 106. The control system 106 is coupled to a monitor 108 that displays an IVUS image (such as an image generated by the IVUS system 100).

In some embodiments, the IVUS catheter 102 is a rotational IVUS catheter, which may be similar to a Revolution® Rotational IVUS Imaging Catheter available from Volcano Corporation and/or rotational IVUS catheters disclosed in U.S. Pat. No. 5,243,988 and U.S. Pat. No. 5,546,948, both of which are incorporated herein by reference in their entirety. The catheter 102 includes an elongated, flexible catheter sheath 110 (having a proximal end portion 114 and a distal end portion 116) shaped and configured for insertion into a lumen of a blood vessel (not shown). A longitudinal axis LA of the catheter 102 extends between the proximal end portion 114 and the distal end portion 116. The catheter 102 is flexible such that it can adapt to the curvature of the blood vessel during use. In that regard, the curved configuration illustrated in FIG. 1 is for exemplary purposes and in no way limits the manner in which the catheter 102 may curve in other embodiments. Generally, the catheter 102 may be configured to take on any desired straight or arcuate profile when in use.

A rotating imaging core 112 extends within the sheath 110. The imaging core 112 has a proximal end portion 118 disposed within the proximal end portion 114 of the sheath 110 and a distal end portion 120 disposed within the distal end portion 116 of the sheath 110. The distal end portion 116 of the sheath 110 and the distal end portion 120 of the imaging core 112 are inserted into the vessel of interest during operation of the IVUS imaging system 100. The usable length of the catheter 102 (for example, the portion that can be inserted into a patient, specifically the vessel of interest) can be any suitable length and can be varied depending upon the application. The proximal end portion 114 of the sheath 110 and the proximal end portion 118 of the imaging core 112 are connected to the interface module 104. The proximal end portions 114, 118 are fitted with a catheter hub 124 that is removably connected to the interface module 104. The catheter hub 124 facilitates and supports a rotational interface that provides electrical and mechanical coupling between the catheter 102 and the interface module 104.

The distal end portion 120 of the imaging core 112 includes a transducer assembly 122. The transducer assembly 122 is configured to be rotated (either by use of a motor or other rotary devices or methods) to obtain images of the vessel. The transducer assembly 122 can be of any suitable type for visualizing a vessel and, in particular, a stenosis in a vessel. In the depicted embodiment, the transducer assembly 122 includes a piezoelectric micromachined ultrasonic transducer ("PMUT") transducer and associated circuitry, such as an application-specific integrated circuit (ASIC). An exemplary PMUT used in IVUS catheters may include a polymer piezoelectric membrane, such as that disclosed in U.S. Pat. No. 6,641,540, hereby incorporated by reference in its entirety. The PMUT transducer can provide greater than 75% bandwidth for optimum resolution in a radial direction, and a spherically-focused aperture for optimum azimuthal and elevation resolution.

The transducer assembly 122 may also include a housing having the PMUT transducer and associated circuitry disposed therein, where the housing has an opening that ultrasound signals generated by the PMUT transducer travel through. Alternatively, the transducer assembly 122 includes a capacitive micromachined ultrasonic transducer ("CMUT"). In yet another alternative embodiment, the transducer assembly 122 includes an ultrasound transducer array (for example, arrays having 16, 32, 64, or 128 elements are utilized in some embodiments).

The rotation of the imaging core 112 within the sheath 110 is controlled by the interface module 104, which provides user interface controls that can be manipulated by a user. The interface module 104 can receive, analyze, and/or display information received through the imaging core 112. It will be appreciated that any suitable functionality, controls, information processing and analysis, and display can be incorporated into the interface module 104. In an example, the interface module 104 receives data corresponding to ultrasound signals (echoes) detected by the imaging core 112 and forwards the received echo data to the control system 106. In an example, the interface module 104 performs preliminary processing of the echo data prior to transmitting the echo data to the control system 106. The interface module 104 may perform amplification, filtering, and/or aggregating of the echo data. The interface module 104 can also supply high- and low-voltage DC power to support operation of the catheter 102 including the circuitry within the transducer assembly 122.

In some embodiments, wires associated with the IVUS imaging system 100 extend from the control system 106 to the interface module 104 such that signals from the control system 106 can be communicated to the interface module 104 and/or vice versa. In some embodiments, the control system 106 communicates wirelessly with the interface module 104. Similarly, it is understood that, in some embodiments, wires associated with the IVUS imaging system 100 extend from the control system 106 to the monitor 108 such that signals from the control system 106 can be communicated to the monitor 108 and/or vice versa. In some embodiments, the control system 106 communicates wirelessly with the monitor 108.

An ultrasound transducer can be included in the IVUS imaging system 100, for example in the transducer assembly 122. The ultrasonic transducer has a small size and achieves a high resolution, so that it is well suited for intravascular imaging. In some embodiments, the ultrasonic transducer has a size on the order of tens or hundreds of microns, can operate in a frequency range between about 1 mega-Hertz (MHz) to about 135 MHz, and can provide sub 50 micron resolution while providing depth penetration of at least 10 millimeters (mm) Furthermore, the ultrasonic transducer is also shaped in a manner to allow a developer to define a target focus area based on a deflection depth of a transducer aperture, thereby generating an image that is useful for defining vessel morphology, beyond the surface characteristics. The various aspects of the ultrasound transducer and its fabrication are discussed in greater detail below.

In certain embodiments, the ultrasound transducer is a piezoelectric micromachined ultrasound transducer (PMUT). In other embodiments, the transducer may include an alternative type of transducer. Additional features can be added in the ultrasound transducer, and some of the features described below can be replaced or eliminated for additional embodiments of the ultrasound transducer. For additional details of fabricating such ultrasonic transducer, refer to U.S. Provisional Application 61/745,212, titled "Methods and Apparatus for Focusing Miniature Ultrasound Transducers" to Dylan Van Hoven, filed on Dec. 21, 2012, Provisional U.S. Patent Application 61/745,091 to Dylan Van Hoven, filed on December 21, entitled "Preparation and Application of a Piezoelectric Film for an Ultrasound Transducer", and Provisional U.S. Patent Application No. 61/646,080 titled "DEVICE AND SYSTEM FOR IMAGING AND BLOOD FLOW VELOCITY MEASUREMENT" filed on May 11, 2012, Provisional U.S. Patent Application No. 61/646,074 titled "ULTRASOUND CATHETER FOR IMAGING AND BLOOD FLOW MEASUREMENT" filed on May 11, 2012, and Provisional U.S. Patent Application No. 61/646,062 titled "Circuit Architectures and Electrical Interfaces for Rotational Intravascular Ultrasound (IVUS) Devices" filed on May 11, 2012, the contents of each of which are hereby incorporated by reference in their entirety.

Traditionally, the ultrasound transducer is located on a wire-die sub assembly, which means that the electrical and mechanical systems are separate sub-assemblies. This leads to problems such as interconnection reliability, higher costs, more complicated fabrication steps, and inflexible configurability.

According to the various aspects of the present disclosure, provided is a method for attaching two electrical dies by wire bonding and then encasing the assembly in a protective casting that works by arranging two dies into a fixture conducive to wire bonding, but also such that doped epoxy may be immediately dispensed over the assembly to form a near-net-shape protective cover, also known as the Drive Can. By doing so, the present disclosure offers numerous advantages over the prior art. Some of these advantages include:
  Mechanical and electrical protection of the ASIC and MEMS interconnection during transport and assembly.
  Eliminate stainless steel can component cost.
  Integrated assembly reduces steps and variation during assembly.
  Allows for both flat and angled transducer arrangements.
  Can be performed at room temperature.

The method steps of the present disclosure are now discussed in more detail in view of FIGS. 2-9, which contain illustrations of the can and wire bonding mixture and casting mold (thereafter referred to as either a bonding apparatus or a bonding fixture). The bonding apparatus may be used to perform wire bonding and molding of a transducer assembly.

Figure 2:
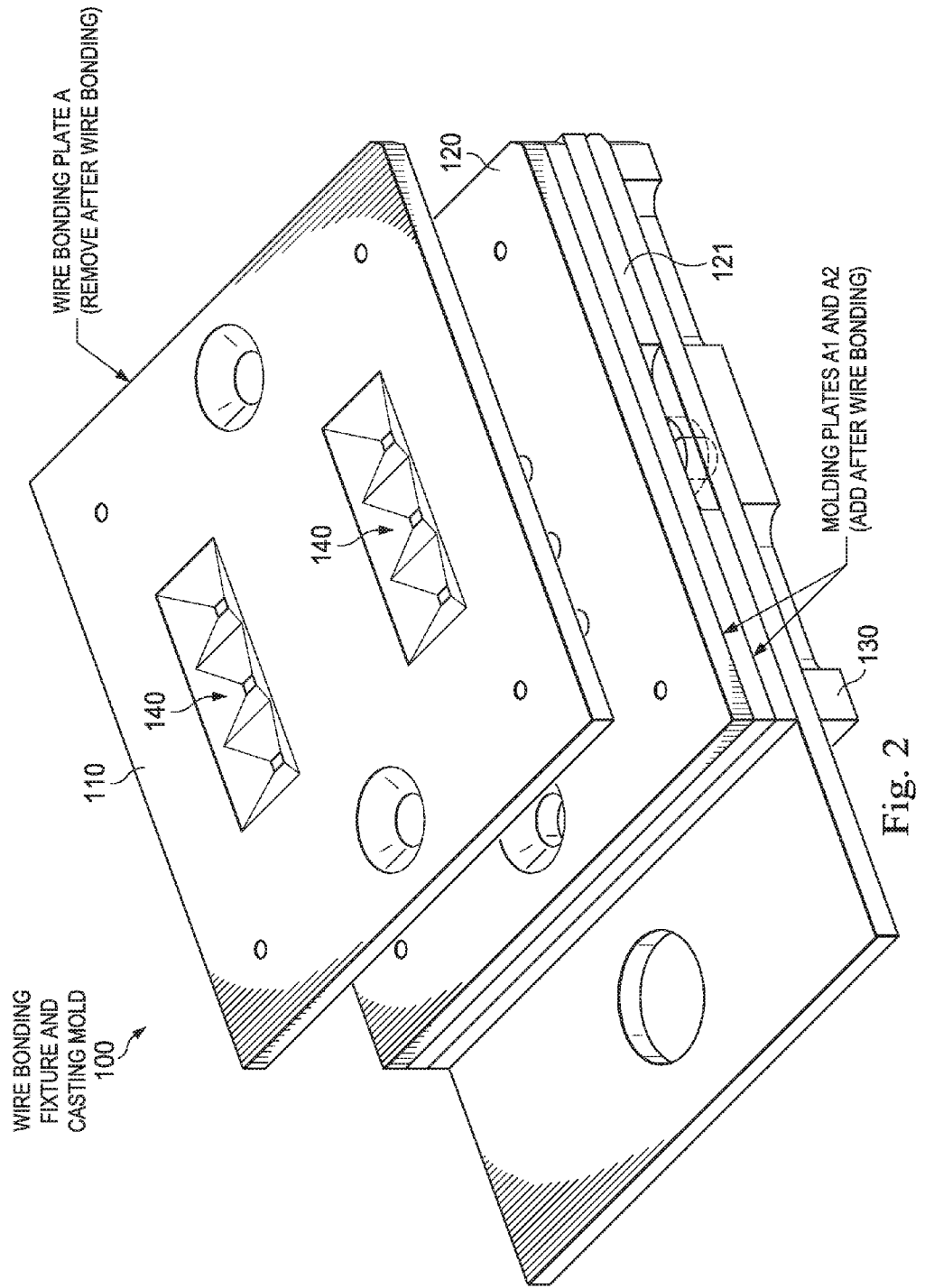
FIGS. 2-5 are various diagrammatic perspective views and cross-sectional views of a bonding apparatus used in transducer fabrication and assembly according to various aspects of the present disclosure.

FIG. 2 is a diagrammatic perspective illustration of the bonding apparatus 100. In the illustrated embodiment, the bonding apparatus 100 includes a bonding plate 110, molding plates 120-121, and a bottom plate 130. The bonding plate 110 or the molding plates 120-121 may be positioned over and against the bottom plate 130 at different stages of fabricating a transducer assembly according to various aspects of the present disclosure.

Figure 3:
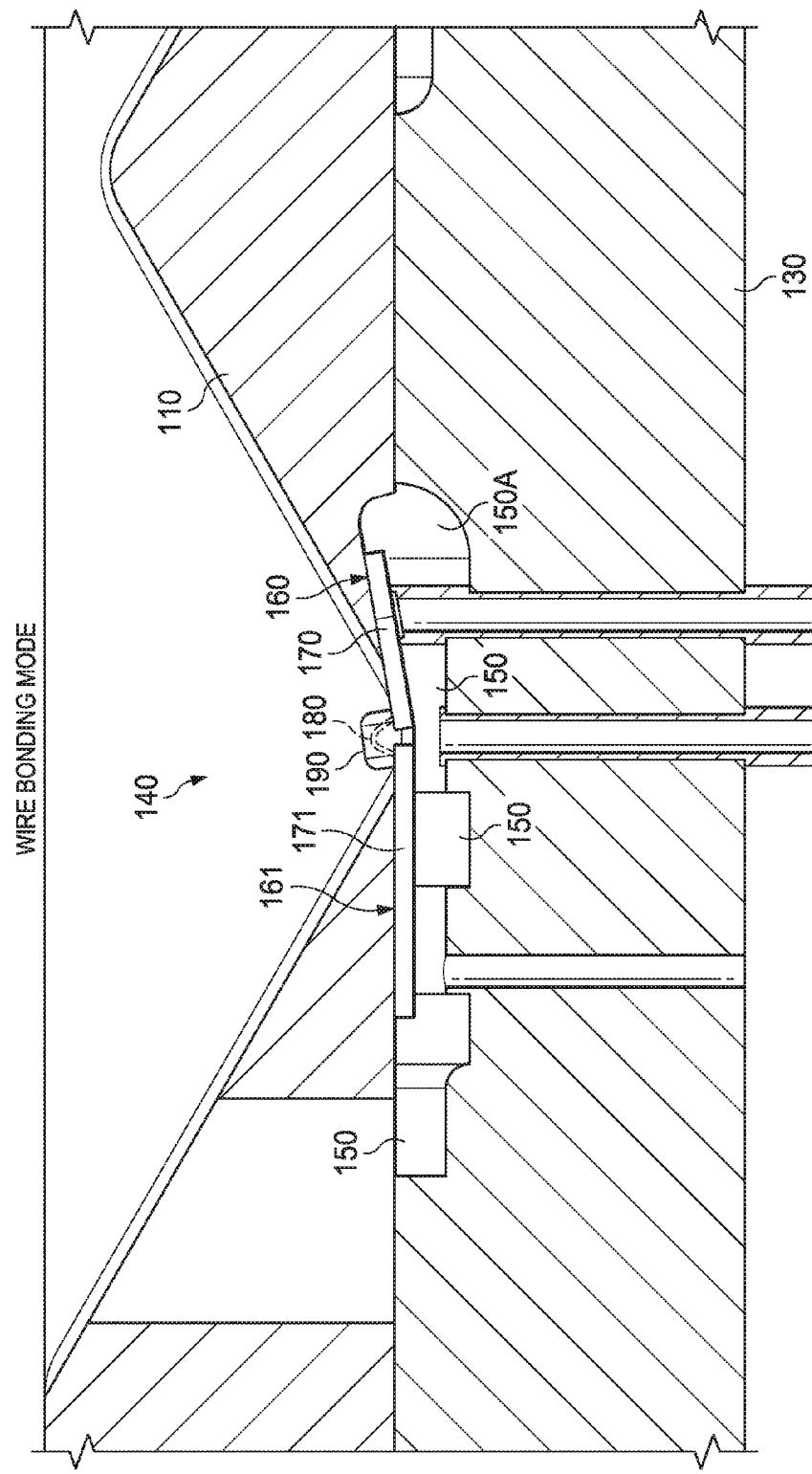

Referring now to FIG. 3, the bonding plate 110 is positioned over and against the bottom plate 130 in a cross-sectional view in a wire bonding stage of fabrication. The molding plates 120-121 are not needed in this stage of fabrication and are thus not shown in FIG. 3. The bonding plate 110 includes a plurality of recesses or openings 140 (also shown in the perspective view of FIG. 2). In the illustrated embodiment, each recess 140 has a sloped profile, that is, a wider opening at the top and a narrower opening at the bottom.

The bottom plate 130 contains a cavity 150. The cavity 150 is shaped as a bottom portion of a transducer assembly. In other words, the cavity 150 partially defines the geometry and shape of the transducer assembly to be formed later. The cavity 150 of the bottom plate 130 also includes a pocket 160 and a pocket 161. The pocket 160 is configured to accommodate a Piezoelectric Micromachined Ultrasound Transducer (PMUT) die 170, and the pocket 161 is configured to accommodate an Application Specific Integrated Circuit (ASIC) die 171. The PMUT is described in detail in U.S. Provisional Application 61/745,212, titled "Methods and Apparatus for Focusing Miniature Ultrasound Transducers" to Dylan Van Hoven, filed on Dec. 21, 2012, Provisional U.S. Patent Application 61/745,091 to Dylan Van Hoven, filed on December 21, entitled "Preparation and Application of a Piezoelectric Film for an Ultrasound Transducer", and Provisional U.S. Patent Application No. 61/646,080 titled "DEVICE AND SYSTEM FOR IMAGING AND BLOOD FLOW VELOCITY MEASUREMENT" filed on May 11, 2012, Provisional U.S. Patent Application No. 61/646,074 titled "ULTRASOUND CATHETER FOR IMAGING AND BLOOD FLOW MEASUREMENT" filed on May 11, 2012, and Provisional U.S. Patent Application No. 61/646,062 titled "Circuit Architectures and Electrical Interfaces for Rotational Intravascular Ultrasound (IVUS) Devices" filed on May 11, 2012, the contents of each of which are hereby incorporated by reference in their entirety. The ASIC die 171 may include a plurality of conductive terminals and electrical circuitry configured to control the operation of the PMUT.

When the bonding plate 110 is pressed against and secured to the bottom plate 130 (for example by a fastening mechanism), the PMUT die 170 and the ASIC die 171 would be trapped in a fixed position in their respective pockets 160 and 161. The recess 140 of the bonding plate 110 exposes a portion of the PMUT die 170 and a portion of the ASIC die 171 (or portions of the pockets 160-161 when they are empty). As such, a conductive element 180 may be attached to both the PMUT die 170 and the ASIC die 171. In this manner, the PMUT die 170 and the ASIC die 171 may be electrically coupled together by the conductive element 180. In the illustrated embodiment, the conductive element 180 is a bond wire. A commercially available wire bonder can be used to electrically attach the dies. Thus, the fabrication stage shown in FIG. 3 may be referred to as a wire bonding mode. It is understood that other conductive elements may be used to implement the conductive element 180 in alternative embodiments.

A thin protective coating 190 is applied over the bond wire (i.e., the conductive element 180 as illustrated herein) to protect the bond wire from later processes, so that the bond wire does not become dislodged. The bonding plate 110 may then be removed. For reasons of simplicity, FIG. 3 illustrates only a single recess 140 and a conductive element 180 being bonded to a respective PMUT die 170 and a respective ASIC die 171. However, it is understood that a plurality of conductive elements may be bonded to a plurality of respective PMUT and ASIC dies simultaneously in this stage of fabrication, since the bonding plate 110 includes a plurality of recesses 140 (e.g., as shown in FIG. 2).

Figure 4:
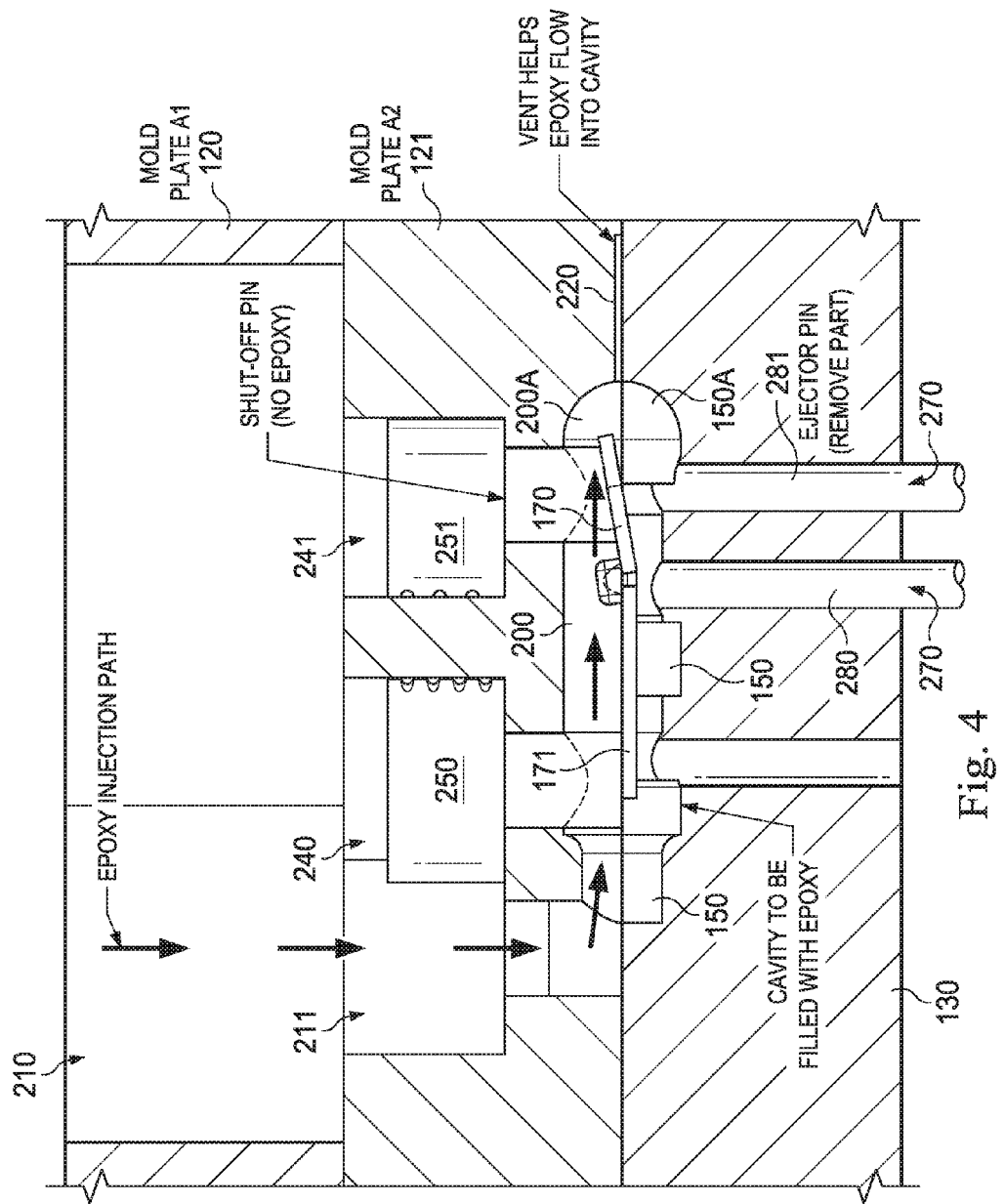

FIG. 4 illustrates a cross-sectional view of the molding plates 120-121 being positioned over and against the bottom plate 130 after the removal of the bonding plate 110. This occurs in a molding stage of the transducer assembly fabrication. As is shown in FIG. 4, the molding plate 120 is positioned over and against the molding plate 121, and the molding plate 121 is positioned over and against the bottom plate 130. The molding plates 120-121 may be secured to the bottom plate 130 by a fastening mechanism. The molding plate 121 includes a cavity 200. The cavity 200 is shaped as a top portion of the transducer assembly. The cavity 200 is aligned with the cavity 150 of the bottom plate 130. Thus, the cavities 150 and 200 collectively define the geometry and shape of the transducer assembly to be formed later. As shown in FIG. 4, portions 150A and 200A of the cavities 150 and 200 also collectively define a curved tip of the transducer assembly. In other words, the tip of the transducer assembly to be formed will have a curved or rounded tip.

The molding plate 120 includes an opening 210, and the molding plate 121 includes an opening 211. The openings 210-211 are vertically aligned with each other, although the opening 211 is narrower than the opening 210 in the illustrated embodiment. The opening 211 is also coupled to the cavity 200. In other words, the opening 211 and the cavity 200 are in fluid communication with one another. The molding plate 121 also includes a vent gap 220 that is coupled to the cavity 200 and in fluid communication with the cavity 200.

Epoxy (or another suitable fluid) may be injected to the cavities 150 and 200 through the openings 210-211. In other words, the epoxy material may flow through the openings 210, 211, and into the cavities 150 and 200, until the cavities 150 and 200 are filled. The vent gap 220 may aid the flow of the epoxy material, for example through a suction force in some embodiments. The injection path is illustrated via the arrows shown in FIG. 4.

Figure 5:
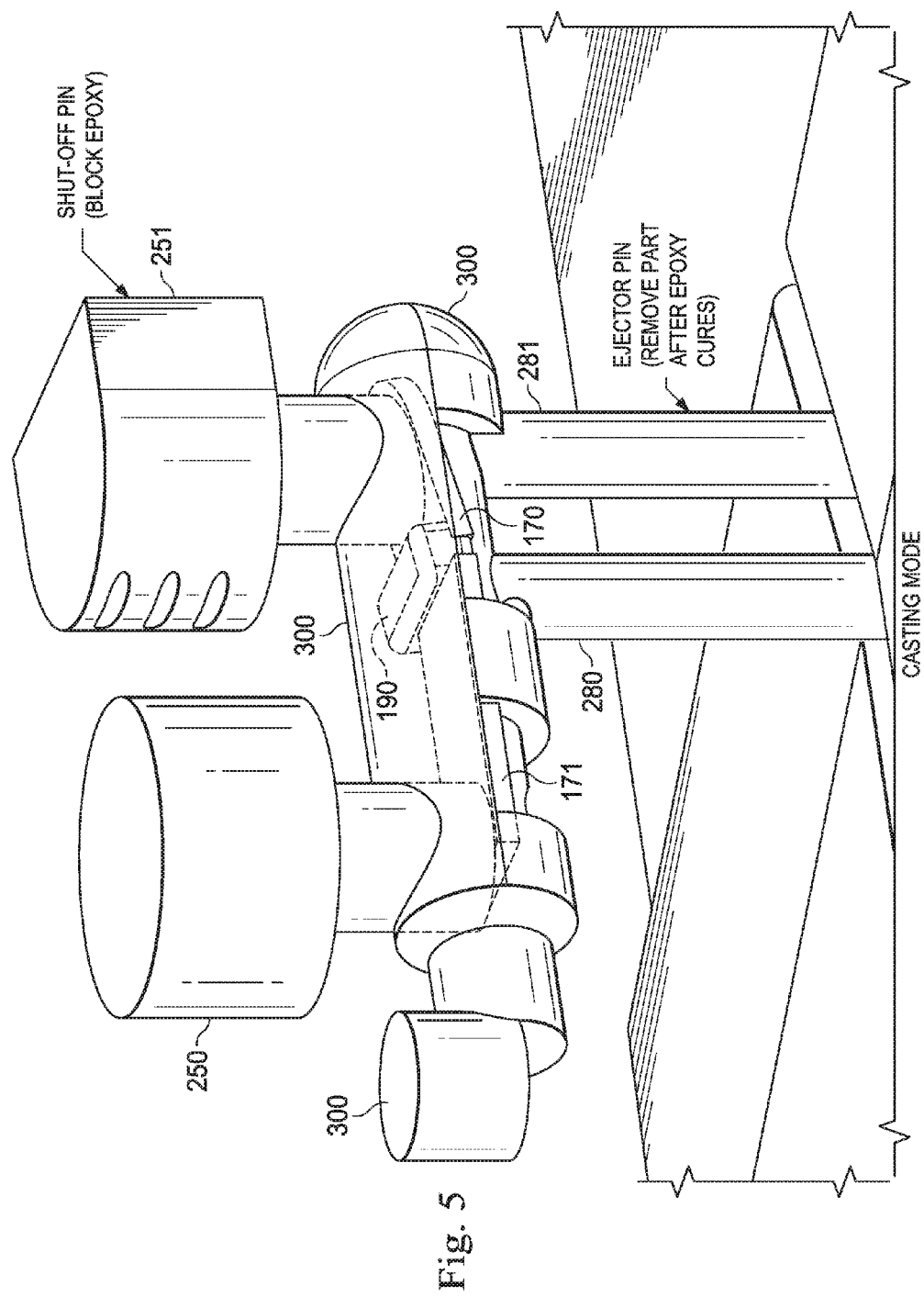

The molding plate 121 also includes an opening 240 that exposes a portion of the pocket that holds the ASIC die 171, as well as an opening 241 that exposes a portion of the pocket that holds the PMUT die 170. These openings 240-241 are filled by shut-off pins 250-251 during the epoxy injection. The shut-off pins 250-251 respectively make physical contact with the top surfaces of the ASIC die 171 and the PMUT die 170 such that the surfaces of the ASIC die 171 and the PMUT die 170 are not exposed to the epoxy during the epoxy injection. A perspective view of the shut-off pins 250-251 is illustrated in FIG. 5.

The epoxy filling the cavities 150 and 200 is then allowed to cure at a high temperature. In some embodiments, the epoxy is cured in an oven at a temperature that is around 0 degrees Celsius for about 2 to 8 hours. The cured epoxy, along with the PMUT die 170 and the ASIC die 171 collectively form a transducer assembly 300 (shown in FIG. 5), which is also referred to as a cast can. The PMUT die 170 and the ASIC die 171 are partially encapsulated or surrounded enclosed by the cured epoxy, which forms a packaging of the transducer assembly. The conductive element (e.g., the bond wire) 180 (shown in FIG. 3) is also encapsulated by the cured epoxy.

The packaging material (i.e., the cured epoxy) has a substantially uniform material composition throughout. The packaging material also supports the PMUT die 170 and the ASIC die 171 in a fixed position relative to each other. The packaging material also defines an outer surface of the ultrasound transducer assembly.

The bottom plate 130 also includes openings 270 and 271 that are coupled to the cavity 150. Ejector pins 280-281 (also shown in FIG. 5) are inserted into the openings 270-271, respectively. After the curing of the epoxy, the molding plates 120-121 are carefully removed. The ejector pins 280-281 may then be used to remove the transducer assembly 300, as shown in FIG. 5.

FIGS. 6-8 illustrate various cross-sectional and perspective views of the transducer assembly 300, the outer shell or surface of which is defined by the packaging material formed by the cured epoxy. As discussed above, the transducer assembly 300 includes a rounded or curved tip 300A. The curved tip 300A is located proximate to the PMUT die 170. In some embodiments, the curved tip 300A has a spherical shape. The transducer assembly 300 also includes recesses 310-311. The recess 310 exposes a portion of the ASIC die 171, and the recess 311 exposes a portion of the PMUT die 170. As discussed above, the recesses 310-311 are formed by the shut-off pins 250-251 occupying the openings 240-241 and coming into physical contact with (and thereby protecting) the ASIC die 171 and the PMUT die 170 during the epoxy injection and curing process.

Figure 9:
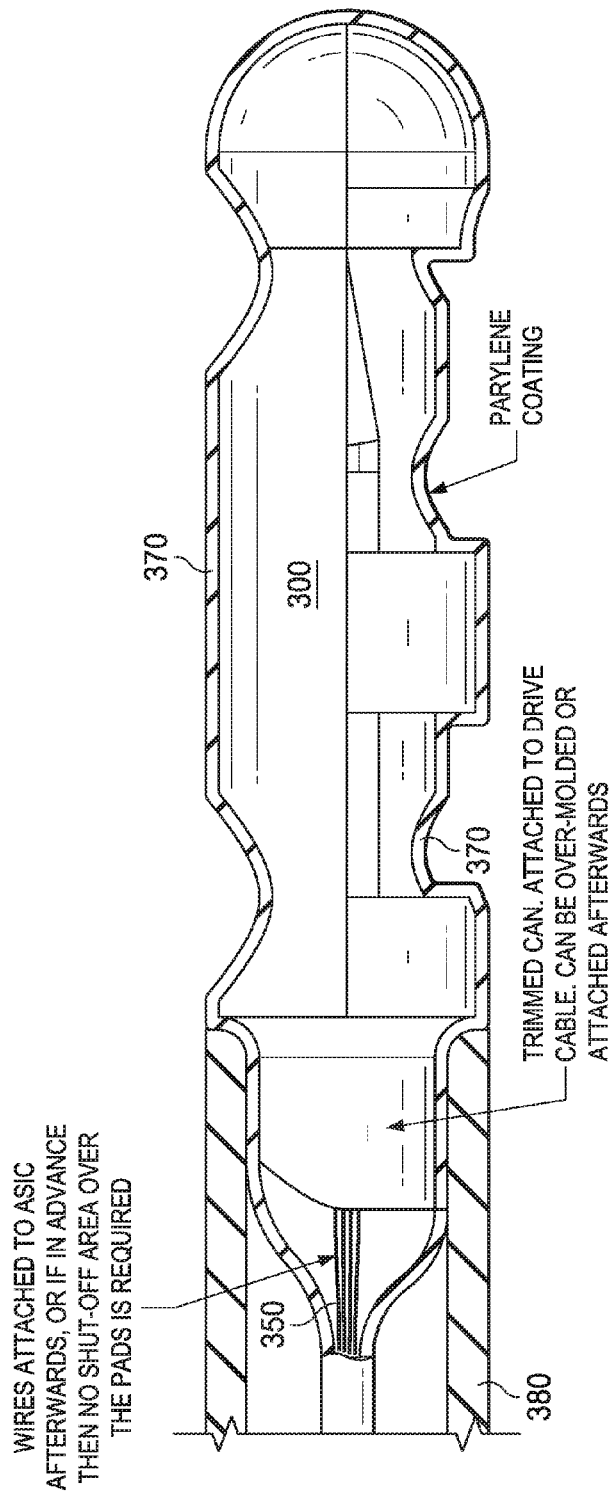

The ASIC die 171 includes conductive terminals 320 (shown in FIG. 8, and also referred to as conductive pads) that are exposed by the recess 310. Referring now to FIG. 9, wires 350 may be welded to the ASIC die 171, for example through the conductive terminals 320. A paralyne coater 370 may then be coated around the transducer assembly 300. The coating may be done in a conformal manner. A drive cable 380 is then glued to the base of the transducer assembly 300. In some embodiments, the wires 350 may also be attached to the ASIC die 171 if a shut-off area over the conductive terminals 320 is not required. In certain alternative embodiments in which the wires 350 are already attached to the ASIC die 171, the drive cable 380 may also be over-molded by the epoxy in the injection molding process.

Among other things, at least the following elements of the present disclosure are believed to be novel:
1. Casting a doped epoxy can over a wire-bonded assembly.
2. Casting a doped epoxy can over an angled wire-bonded assembly.
3. Using shut-off pins to protect the transducer surface and cable attachment pads.
4. Using high lubricity plating on the tool to insure easy ejection.
5. Using ejector pins to separate the case part from the tool.
6. Using a distal vent to draw epoxy into the tool. (A vacuum may be applied.)
7. Conformal coating the cast epoxy can.
8. Attaching the cast can to a Drive Cable.

Figure 10:
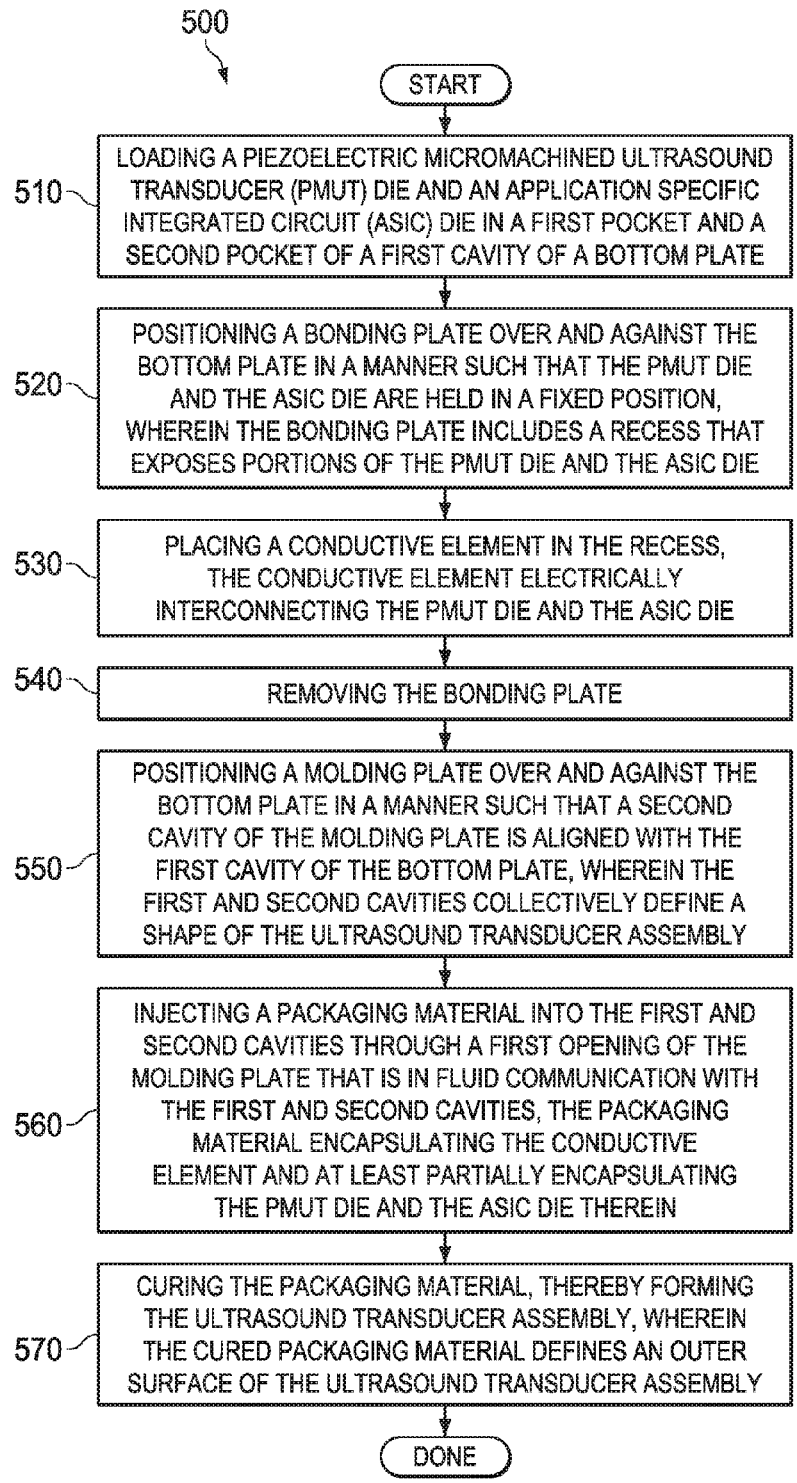
FIG. 10 is a flowchart of a method of fabricating an ultrasound transducer assembly according to various aspects of the present disclosure.

FIG. 10 is a flowchart of a method 500 of fabricating an ultrasound transducer assembly. The method 500 includes a step 510 of loading a Piezoelectric Micromachined Ultrasound Transducer (PMUT) die and an Application Specific Integrated Circuit (ASIC) die in a first pocket and a second pocket of a first cavity of a bottom plate. The method 500 includes a step 520 of positioning a bonding plate over and against the bottom plate in a manner such that the PMUT die and the ASIC die are held in a fixed position. The bonding plate includes a recess that exposes portions of the PMUT die and the ASIC die. The method 500 includes a step 530 of placing a conductive element in the recess. The conductive element electrically interconnects the PMUT die and the ASIC die. The method 500 includes a step 540 of removing the bonding plate. The method 500 includes a step 550 of positioning a molding plate over and against the bottom plate in a manner such that a second cavity of the molding plate is aligned with the first cavity of the bottom plate. The first and second cavities collectively define a shape of the ultrasound transducer assembly. The method 500 includes a step 560 of injecting a packaging material into the first and second cavities through a first opening of the molding plate that is in fluid communication with the first and second cavities. The packaging material encapsulates the conductive element and at least partially encapsulating the PMUT die and the ASIC die therein. The method 500 includes a step 570 of curing the packaging material, thereby forming the ultrasound transducer assembly, wherein the cured packaging material defines an outer surface of the ultrasound transducer assembly.

In some embodiments, the packaging material comprises epoxy. In some embodiments, the molding plate includes a second opening that exposes a portion of the PMUT die when the molding plate is positioned against the bottom plate. The method 500 may further include a step of placing a shut-off pin in the second opening during the injecting so as to prevent the packaging material from coming into contact with a surface of the PMUT die. In some embodiments, the molding plate includes a third opening that exposes a portion of the ASIC die when the molding plate is positioned against the bottom plate. The method 500 may further include a step of placing a further shut-off pin in the third opening during the injecting so as to prevent the packaging material from coming into contact with a surface of the ASIC die. In some embodiments, the step 530 of placing the conductive element comprises wire-bonding the PMUT die and the ASIC die. In some embodiments, the method 500 further includes a step of applying a protective coating around the conductive element in the recess before the removing of the bonding plate. In some embodiments, the method 500 further includes the following steps: removing the transducer assembly; applying a paralyne coating around the transducer assembly; and attaching the transducer assembly to a drive cable.

One aspect of the present disclosure involves a bonding apparatus for bonding a plurality of electrical dies. The bonding apparatus includes: a bottom plate that includes a first cavity, wherein the first cavity includes a first pocket configured to accommodate a Piezoelectric Micromachined Ultrasound Transducer (PMUT) die and a second pocket configured to accommodate an Application Specific Integrated Circuit (ASIC) die; a bonding plate configured to be positioned over and against the bottom plate, the bonding plate including a recess, wherein when the bonding plate is positioned against the bottom plate: the PMUT die and the ASIC die would be trapped in a fixed position; and the recess exposes a portion of the first pocket and a portion of the second pocket; a molding plate configured to be positioned over and against the bottom plate, wherein the molding plate includes: a second cavity that is aligned with the first cavity when the molding plate is positioned against the bottom plate, such that the first and second cavities collectively define a shape of a transducer assembly; a first opening that is coupled to the second cavity, wherein the first opening exposes a portion of the first pocket when the molding plate is positioned against the bottom plate; a second opening that is coupled to the second cavity, wherein the second opening exposes a portion of the second pocket when the molding plate is positioned against the bottom plate; and a third opening that is in fluid communication with the first and second cavities such that a fluid can flow into the first and second cavities through the third opening.

In some embodiments, the bonding apparatus further includes a first shut-off pin configured to be positioned inside the first opening of the molding plate such that, when the molding plate is positioned against the bottom plate, the first shut-off pin makes physical contact with an upper surface of the PMUT die.

In some embodiments, the bonding apparatus further includes a second shut-off pin configured to be positioned inside the second opening of the molding plate such that, when the molding plate is positioned against the bottom plate, the second shut-off pin makes physical contact with an upper surface of the ASIC die.

In some embodiment, the molding plate further includes a vent gap that is in fluid communication with the second cavity.

In some embodiments, the molding plate is a first molding plate, and further comprising a second molding plate that is configured to be positioned over and against the first molding plate, wherein the second molding plate includes a fourth opening that is in fluid communication with the third opening.

In some embodiments, the transducer assembly has a curved tip.

In some embodiments, the curved tip is located proximate to the PMUT die and has a spherical shape.

In some embodiments, the recess of the bonding plate is configured to allow for an electrical connection between the PMUT die and the ASIC die.

In some embodiments, the electrical connection comprises a bond wire.

Another aspect of the present disclosure involves an ultrasound transducer assembly. The ultrasound transducer assembly includes: a Piezoelectric Micromachined Ultrasound Transducer (PMUT) die that includes a PMUT device; an Application Specific Integrated Circuit (ASIC) die that is physically separated from the PMUT die, the ASIC die including a plurality of conductive terminals; a conductive element that electrically couples the PMUT die and the ASIC die together; a packaging material that encapsulates the conductive element and partially encapsulates the PMUT die and the ASIC die therein, wherein the packaging material has a substantially uniform material composition throughout and includes a first opening that exposes a surface of the PMUT device, and wherein the packaging material supports the PMUT die and the ASIC die in a fixed position relative to each other and defines an outer surface of the ultrasound transducer assembly.

In some embodiments, the packaging material is epoxy.

In some embodiments, the conductive element comprises a bond wire.

In some embodiments, the ultrasound transducer assembly of claim further includes a protective layer coated around the bond wire.

In some embodiments, the ultrasound transducer assembly further includes a layer conformally coated around the packaging material.

In some embodiments, the layer contains paralyne.

In some embodiments, the ultrasound transducer assembly further includes wires attached to a drive cable, wherein the wires are electrically coupled to the ASIC die.

In some embodiments, the packaging material includes a second opening that at least partially exposes the conductive terminals.

In some embodiments, the packaging material has a rounded tip near the PMUT die.

Another aspect of the present disclosure involves a method of fabricating an ultrasound transducer assembly. The method includes: loading a Piezoelectric Micromachined Ultrasound Transducer (PMUT) die and an Application Specific Integrated Circuit (ASIC) die in a first pocket and a second pocket of a first cavity of a bottom plate; positioning a bonding plate over and against the bottom plate in a manner such that the PMUT die and the ASIC die are held in a fixed position, wherein the bonding plate includes a recess that exposes portions of the PMUT die and the ASIC die; placing a conductive element in the recess, the conductive element electrically interconnecting the PMUT die and the ASIC die; thereafter removing the bonding plate; positioning a molding plate over and against the bottom plate in a manner such that a second cavity of the molding plate is aligned with the first cavity of the bottom plate, wherein the first and second cavities collectively define a shape of the ultrasound transducer assembly; injecting a packaging material into the first and second cavities through a first opening of the molding plate that is in fluid communication with the first and second cavities, the packaging material encapsulating the conductive element and at least partially encapsulating the PMUT die and the ASIC die therein; and curing the packaging material, thereby forming the ultrasound transducer assembly, wherein the cured packaging material defines an outer surface of the ultrasound transducer assembly.

In some embodiments, the packaging material comprises epoxy.

In some embodiments, the molding plate includes a second opening that exposes a portion of the PMUT die when the molding plate is positioned against the bottom plate, and further comprising: placing a shut-off pin in the second opening during the injecting so as to prevent the packaging material from coming into contact with a surface of the PMUT die.

In some embodiments, the molding plate includes a third opening that exposes a portion of the ASIC die when the molding plate is positioned against the bottom plate, and further comprising: placing a further shut-off pin in the third opening during the injecting so as to prevent the packaging material from coming into contact with a surface of the ASIC die.

In some embodiments, the step of placing the conductive element comprises wire-bonding the PMUT die and the ASIC die.

In some embodiments, the method further includes a step of applying a protective coating around the conductive element in the recess before the removing of the bonding plate.

In some embodiments, the method further includes the following steps: removing the transducer assembly; applying a paralyne coating around the transducer assembly; and attaching the transducer assembly to a drive cable.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A manufacturing apparatus, comprising:
a bottom plate that includes a first cavity, wherein the first cavity includes a first pocket configured to accommodate a Piezoelectric Micromachined Ultrasound Transducer (PMUT) die and a second pocket configured to accommodate an Application Specific Integrated Circuit (ASIC) die;
a bonding plate configured to be removably positioned over and against the bottom plate, the bonding plate including a recess, wherein when the bonding plate is positioned against the bottom plate:
the PMUT die and the ASIC die would be trapped in a fixed position; and
the recess exposes a portion of the first pocket and a portion of the second pocket;
a molding plate configured to be removably positioned over and against the bottom plate, wherein the molding plate includes:
a second cavity that is aligned with the first cavity when the molding plate is positioned against the bottom plate, such that the first and second cavities collectively define a shape of a transducer assembly;
a first opening that is coupled to the second cavity, wherein the first opening exposes a portion of the first pocket when the molding plate is positioned against the bottom plate;
a second opening that is coupled to the second cavity, wherein the second opening exposes a portion of the second pocket when the molding plate is positioned against the bottom plate; and
a third opening that is in fluid communication with the first and second cavities such that a fluid can flow into the first and second cavities through the third opening; and
a first shut-off pin configured to be removably positioned inside the first opening of the molding plate such that, when the molding plate is positioned against the bottom plate, the first shut-off pin makes physical contact with an upper surface of the PMUT die.

2. The bonding apparatus of claim 1, further comprising a second shut-off pin configured to be removably positioned inside the second opening of the molding plate such that, when the molding plate is positioned against the bottom plate, the second shut-off pin makes physical contact with an upper surface of the ASIC die.

3. The bonding apparatus of claim 1, wherein the molding plate further includes a vent gap that is in fluid communication with the second cavity.

4. The bonding apparatus of claim 1, wherein the molding plate is a first molding plate, and further comprising a second molding plate that is configured to be positioned over and against the first molding plate, wherein the second molding plate includes a fourth opening that is in fluid communication with the third opening.

5. The bonding apparatus of claim 1, wherein the transducer assembly has a curved tip.

6. The bonding apparatus of claim 5, wherein the curved tip is located proximate to the PMUT die and has a spherical shape.

7. The bonding apparatus of claim 1, wherein the recess of the bonding plate is configured to allow for an electrical connection between the PMUT die and the ASIC die.

8. The bonding apparatus of claim 7, wherein the electrical connection comprises a bond wire.

9. A manufacturing system, comprising:
a base plate having a first cavity, the first cavity including a first section sized and shaped to receive an ultrasound transducer die and a second section sized and shaped to receive an Application Specific Integrated Circuit (ASIC) die;
a bonding plate sized and shaped to be removably positioned over and against the base plate during a bonding stage, the bonding plate including a recess such that when the bonding plate is positioned over and against the base plate the ultrasound transducer die and the ASIC die are maintained in a fixed position and a portion of the first section and a portion of the second section are exposed by the recess; and
a molding plate sized and shaped to be removably positioned over and against the base plate during a molding stage, the molding plate including a second cavity and a plurality of openings in communication with the second cavity such that when the molding plate is positioned over and against the base plate the plurality of openings:
expose at least a portion of the first section of the first cavity,
expose at least a portion of the second section of the first cavity; and
provide a fluid pathway to a space defined by the first and second cavities; and
a first shut-off pin configured to be removably positioned within at least one of the plurality of openings of the molding plate, wherein the first shut-off pin is sized and shaped to physically contact an upper surface of the ultrasound transducer die when the molding plate is positioned over and against the base plate.

10. The bonding system of claim 9, further comprising a second shut-off pin sized and shaped to physically contact an upper surface of the ASIC die when the molding plate is positioned over and against the base plate.

11. The bonding system of claim 9, wherein the molding plate further includes a vent gap in fluid communication with the second cavity.

12. The bonding system of claim 9, wherein the molding plate is a first molding plate, and further comprising a second molding plate sized and shaped to be positioned over and against the first molding plate, wherein the second molding plate includes at least one opening.

13. The bonding system of claim 12, wherein the at least one opening of the second molding plate is in fluid communication with the fluid pathway to the space defined by the first and second cavities when the second molding plate is positioned over and against the first molding plate and the first molding plate is positioned over and against the base plate.

14. The bonding system of claim 9, wherein the recess of the bonding plate is sized and shaped to facilitate formation of an electrical connection between the PMUT die and the ASIC die.

15. The bonding system of claim 14, wherein the electrical connection comprises a wire bond.

16. The bonding system of claim 9, wherein the plurality of openings comprises a first opening, a second opening, and a third opening.

17. The bonding system of claim 16, wherein:
the first opening is sized and shaped to expose the at least a portion of the first section of the first cavity;
the second opening is sized and shaped to expose the at least a portion of the second section of the first cavity; and
the third opening is sized and shaped to provide the fluid pathway to the space defined by the first and second cavities.

18. The bonding system of claim 9, wherein the space defined by the first and second cavities defines a transducer assembly shape.

19. The bonding system of claim 18, wherein the transducer assembly shape includes a rounded tip.

20. The bonding system of claim 19, wherein the first cavity defines a first portion of the rounded tip and the second cavity defines a second portion of the rounded tip.

* * * * *